(12) United States Patent
Li et al.

(10) Patent No.: US 11,166,968 B2
(45) Date of Patent: Nov. 9, 2021

(54) SYNERGISTIC COMPOSITION FOR MAINTENANCE OF HEALTHY BALANCE OF MICROFLORA

(71) Applicant: KIMBERLY-CLARK WORLDWIDE, INC., Neenah, WI (US)

(72) Inventors: Jingru Li, Milton, GA (US); Lindsay Adrienne Peed, Peachtree Corners, GA (US); Cheryce Francina Joyner, Tallahassee, FL (US); Rebecca Ann Vongsa, Neenah, WI (US); David William Koenig, Menasha, WI (US); Ryan Daniel Bartell, Appleton, WI (US); Paige Nicole Hollmaier, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/758,535

(22) PCT Filed: Sep. 29, 2015

(86) PCT No.: PCT/US2015/052956
§ 371 (c)(1),
(2) Date: Mar. 8, 2018

(87) PCT Pub. No.: WO2017/058175
PCT Pub. Date: Apr. 6, 2017

(65) Prior Publication Data
US 2018/0250318 A1 Sep. 6, 2018

(51) Int. Cl.
| | |
|---|---|
| *A61K 31/7004* | (2006.01) |
| *A61K 31/194* | (2006.01) |
| *A61K 31/7016* | (2006.01) |
| *A61K 31/724* | (2006.01) |
| *A61K 31/70* | (2006.01) |
| *A61P 15/02* | (2006.01) |
| *A61K 9/00* | (2006.01) |
| *A61K 31/732* | (2006.01) |
| *A61K 31/733* | (2006.01) |

(52) U.S. Cl.
CPC ........ *A61K 31/7004* (2013.01); *A61K 9/0034* (2013.01); *A61K 31/194* (2013.01); *A61K 31/70* (2013.01); *A61K 31/7016* (2013.01); *A61K 31/724* (2013.01); *A61P 15/02* (2018.01); *A61K 31/732* (2013.01); *A61K 31/733* (2013.01); *A61K 2300/00* (2013.01); *Y02A 50/30* (2018.01)

(58) Field of Classification Search
CPC ............ A61K 31/7004; A61K 31/7016; A61K 9/0034; A61K 31/724; A61K 2300/00; A61P 15/02

USPC .......................................................... 514/53
See application file for complete search history.

(56) References Cited

U.S. PATENT DOCUMENTS

| | | | |
|---|---|---|---|
| 5,171,575 A | * | 12/1992 | Shibata ................. A23K 10/18 424/439 |
| 5,176,911 A | | 1/1993 | Tosi |
| 5,451,402 A | | 9/1995 | Allen |
| 5,466,463 A | | 11/1995 | Ford |
| 5,518,733 A | | 5/1996 | Lamothe |
| 5,801,116 A | | 9/1998 | Cottrell et al. |
| 5,958,104 A | | 9/1999 | Nonomura |
| 5,994,326 A | * | 11/1999 | Matsuda .............. A61K 31/702 514/61 |
| 6,159,465 A | | 12/2000 | Adlerberth |
| 6,372,209 B1 | | 4/2002 | Chrisope |
| 6,432,440 B1 | | 8/2002 | Watts |
| 6,468,526 B2 | | 10/2002 | Chrisope |
| 6,632,796 B1 | | 10/2003 | Zeng |
| 6,716,435 B1 | | 4/2004 | Farmer |
| 6,899,890 B2 | | 5/2005 | Kirschner |
| 6,964,949 B2 | | 11/2005 | Zeng |
| 6,967,949 B2 | | 11/2005 | Davis et al. |
| 7,179,458 B2 | | 2/2007 | Chang |
| 7,182,954 B1 | | 2/2007 | Cote et al. |
| 7,312,067 B2 | | 12/2007 | Samuelsson |

(Continued)

FOREIGN PATENT DOCUMENTS

| | | |
|---|---|---|
| CA | 2490016 | 12/2004 |
| CN | 1451389 A * | 10/2003 |

(Continued)

OTHER PUBLICATIONS

MicrobeWiki; Oct. 26, 2014.*

(Continued)

*Primary Examiner* — Shaojia A Jiang
*Assistant Examiner* — Michael C Henry
(74) *Attorney, Agent, or Firm* — Kimberly-Clark Worldwide, Inc.

(57) ABSTRACT

The present invention relates to compositions, particularly compositions useful in maintaining and supporting healthy microflora in the female urogenital tract which could lead to inhibition of vaginal infections, as well as methods of treating and preventing vaginal infections. Compositions useful in supporting healthy microflora, disclosed herein, generally comprise a therapeutic amount of a first saccharide and a therapeutic amount of a second saccharide or an organic acid. The saccharides may be, for example, a pentose, a disaccharide, a cyclodextrin, a pectic substance or a non-digestible polysaccharide. The organic acid may be, for example, malic acid.

4 Claims, No Drawings

(56) References Cited

U.S. PATENT DOCUMENTS

| | | | |
|---|---|---|---|
| 7,507,402 | B1 | 3/2009 | Farmer |
| 7,619,008 | B2 | 11/2009 | Yang |
| 7,713,726 | B2 | 5/2010 | Farmer |
| 7,786,176 | B2 | 8/2010 | Martin |
| 8,137,706 | B2 | 3/2012 | Al-Ghazzewi |
| 8,178,746 | B2 | 5/2012 | Hildeberg |
| 8,222,020 | B2 | 7/2012 | Brusk |
| 8,258,250 | B2 | 9/2012 | Fevola |
| 8,277,799 | B2 | 10/2012 | Farmer |
| 8,445,226 | B2 | 5/2013 | Garner |
| 8,460,917 | B2 | 6/2013 | Brondstad |
| 8,551,518 | B2 | 10/2013 | Marsh et al. |
| 8,586,549 | B2 | 11/2013 | Zhou |
| 8,609,630 | B2 | 12/2013 | Brown |
| 8,632,766 | B2 | 1/2014 | Heczko |
| 8,642,029 | B2 | 2/2014 | Wang |
| 8,703,179 | B2 | 4/2014 | Boga |
| 8,821,854 | B2 | 9/2014 | Farmer |
| 8,853,382 | B2 | 10/2014 | Hammarstrom |
| 8,871,244 | B2 | 10/2014 | Andersch |
| 8,906,668 | B2 | 12/2014 | Henn |
| 8,961,945 | B2 | 2/2015 | Fevola |
| 2002/0090365 | A1 | 7/2002 | Chrisope |
| 2005/0064527 | A1 | 3/2005 | Levy |
| 2005/0175630 | A1 | 8/2005 | Raz |
| 2005/0175640 | A1* | 8/2005 | Yamada .......... A61K 31/56 424/400 |
| 2005/0276836 | A1 | 12/2005 | Wilson |
| 2006/0067921 | A1* | 3/2006 | Conway .......... A61K 35/747 424/93.45 |
| 2006/0105963 | A1 | 5/2006 | Yang et al. |
| 2006/0154874 | A1 | 7/2006 | Hansen |
| 2007/0111965 | A1 | 5/2007 | Kipp |
| 2007/0286893 | A1 | 12/2007 | Marsh et al. |
| 2008/0107776 | A1 | 5/2008 | Prakash et al. |
| 2008/0206188 | A1 | 8/2008 | Alverdy |
| 2008/0300558 | A1 | 12/2008 | Brusk |
| 2009/0028839 | A1 | 1/2009 | Tchikindas |
| 2009/0036849 | A1 | 2/2009 | Gustafson |
| 2009/0291069 | A1 | 11/2009 | Mastrodonato |
| 2010/0055153 | A1 | 3/2010 | Majmudar |
| 2011/0105448 | A1 | 5/2011 | Dhuppad |
| 2011/0118686 | A1 | 5/2011 | Vega et al. |
| 2011/0124594 | A1 | 5/2011 | Antoun |
| 2012/0027838 | A1 | 2/2012 | Gordon |
| 2012/0058181 | A1 | 3/2012 | Currie |
| 2012/0172831 | A1 | 7/2012 | Darcy |
| 2012/0201796 | A1 | 8/2012 | Beasley |
| 2012/0258126 | A1 | 10/2012 | Scholler |
| 2013/0022586 | A1 | 1/2013 | Versalovic |
| 2014/0017340 | A1 | 1/2014 | Choi |
| 2014/0037758 | A1 | 2/2014 | Choi et al. |
| 2014/0273144 | A1 | 9/2014 | Hawkins |
| 2015/0004225 | A1 | 1/2015 | Pillay |
| 2015/0018353 | A1 | 1/2015 | Kim |
| 2015/0223466 | A1 | 8/2015 | Malefyt |
| 2016/0243172 | A1 | 8/2016 | Cook |
| 2020/0085994 | A1 | 3/2020 | Vega et al. |

FOREIGN PATENT DOCUMENTS

| | | |
|---|---|---|
| CN | 1761406 A | 4/2006 |
| CN | 1984990 A | 6/2007 |
| CN | 1802101 B | 4/2010 |
| CN | 102123736 A | 7/2011 |
| CN | 102370598 A | 3/2012 |
| CN | 102870987 A | 1/2013 |
| CN | 103255679 A | 8/2013 |
| CN | 103053900 B | 4/2016 |
| DE | 3510531 A1 | 10/1986 |
| EP | 0257007 A1 | 2/1988 |
| EP | 0773781 B1 | 10/2003 |
| EP | 1481666 A1 | 12/2004 |
| EP | 1633857 A2 | 3/2006 |
| EP | 1946760 A1 | 7/2008 |
| EP | 2314283 A1 | 4/2011 |
| EP | 2353601 B1 | 9/2015 |
| IN | 00404MU2002 A | 2/2004 |
| JP | 63309269 A | 12/1988 |
| JP | 2000189109 A * | 7/2000 |
| JP | 2004026725 A | 1/2004 |
| JP | 2006191830 A | 7/2006 |
| JP | 2009517030 A | 4/2009 |
| JP | 4553604 B2 | 9/2010 |
| JP | 2011157348 A | 8/2011 |
| JP | 2013018757 A | 1/2013 |
| KR | 20140046462 A | 4/2014 |
| RU | 2473347 C1 | 1/2013 |
| WO | 9729762 A1 | 8/1997 |
| WO | 9729763 A1 | 8/1997 |
| WO | 9846261 A1 | 10/1998 |
| WO | WO-9846206 A1 * | 10/1998 .......... A61K 8/44 |
| WO | 04052121 A1 | 6/2004 |
| WO | 04064850 A1 | 8/2004 |
| WO | 04076615 A2 | 9/2004 |
| WO | 05060937 A1 | 7/2005 |
| WO | 05087270 A1 | 9/2005 |
| WO | 05112567 A2 | 12/2005 |
| WO | 06005464 A2 | 1/2006 |
| WO | WO-2006000421 A2 * | 1/2006 .......... A61K 31/00 |
| WO | 06030100 A1 | 3/2006 |
| WO | 06134409 A2 | 12/2006 |
| WO | 07117175 A1 | 10/2007 |
| WO | 08100375 A2 | 8/2008 |
| WO | 10056685 A2 | 5/2010 |
| WO | 10061284 A2 | 6/2010 |
| WO | 10062707 A1 | 6/2010 |
| WO | 10108314 A1 | 9/2010 |
| WO | 11005756 A1 | 1/2011 |
| WO | 11041938 A1 | 4/2011 |
| WO | 12077038 A1 | 6/2012 |
| WO | 12101500 A1 | 8/2012 |
| WO | 14012805 A1 | 1/2014 |
| WO | 14026707 A1 | 2/2014 |
| WO | 14027006 A1 | 2/2014 |
| WO | 14106541 A1 | 7/2014 |
| WO | 14113693 A1 | 7/2014 |
| WO | 15135470 A1 | 9/2015 |
| WO | 16149687 A1 | 9/2016 |

OTHER PUBLICATIONS

Domagk et al. (J. Biol. Chem. 1958, 233:283-286).*
Fulcher CA, SRI International ; Jun. 25, 2013.*
Yamada et al.; CN 1451389 A; Oct. 29, 2003 (Machine-English Translation).*
Goto et al.; JP 2000189109 A; Jul. 11, 2000 (Machine-English Translation).*
Van Zanten G.C. et al. The effect of selected synbiotics on microbial composition and short-chain fatty acid production in a model system of the human colon // PLoS One.—2012.
Ojala T. et al. Genome Sequence of Lactobacillus crispatus ST1 // Journal of Bacteriology, 2010, vol. 192, No. 13, pp. 3547-3548.
Hartemink, Ralf, "Prebiotic effects of non-digestible oligo- and polysaccharides", 1999, Agricultural University. Promotor(en): F.M. Rombouts; M.J.R. Nout.—S.l. : S.n.—ISBN 9789058080516—205, https://library.wur.nl/WebQuery/wurpubs/fulltext/196578.
Karlton-Senaye, B. et al., "Synergistic Effect of Polysaccharide Gums and Antimicrobial Agents on Susceptiblity and Protein Expression of Select Pathogenic Microorganisms in Milk", Journal of Food Research, 2018, vol. 7, No. 2, pp. 35-53. (Year: 2018).
Thitaram, Sutawee Narint, "The effect of isomaltooligosaccharide on *Bifidobacterium* spp. population in young broiler chickens", 2004, Doctoral dissertation, University of Georgia, https://getd.libs.uga.edu/pdfs/thitaram_sutawee_n_200408_ms.pdf.
Copending U.S. Appl. No. 15/758,548, filed Mar. 8, 2018, by Li et al. for "Composition for Maintaining Lactobacillus Dominance".
Copending US Patent Application No. PCT/US17/19833 filed Feb. 28, 2017, by Li et al. for "Synergistic Composition for Maintenance of Healthy Balance of Microflora".

(56) References Cited

OTHER PUBLICATIONS

Chang, C. E. et al., "Cultivation of Lactobacillus crispatus KLB46 isolated from human vagina", Biotechnology and Bioprocess Engineering, 2001, vol. 6, pp. 128-132, See the whole document.

* cited by examiner

SYNERGISTIC COMPOSITION FOR MAINTENANCE OF HEALTHY BALANCE OF MICROFLORA

BACKGROUND OF THE DISCLOSURE

Humans are colonized by microbes in the gastrointestinal tract, on the skin, and in other epithelial and tissue niches such as the oral cavity, eye surface and vagina. In healthy persons a single local or tissue type may be inhabited by hundreds of different species of bacteria. Interactions between various bacteria species in these populations and between bacteria and the human host shape the community structure with availability of and competition for resources affecting the distribution of various species of bacteria. Such resources may be food, location and the availability of space to grow or a physical structure to which the bacteria may attach.

A healthy microbial flora provides the host with multiple benefits, including colonization resistance to a broad spectrum of pathogens, essential nutrient biosynthesis and absorption, and immune stimulation. For example, a normal vagina generally contains more than about $10^4$ lactobacilli per milliliter of vaginal fluid. Under normal conditions, the vagina flora provides a mildly acidic environment that helps guard against the invasion of pathogenic microbes. Unfortunately, this vaginal balance may be easily upset by a variety of external factors that ultimately lead to vaginal infection. Vaginal infection is a clinical syndrome and exists in three primary forms, i.e., bacterial vaginosis, candidal vaginitis ("yeast"), and *trichomonas* vaginitis ("trich").

Current treatment regimens for bacterial infection of the vagina involve the use of various broad spectrum antibiotics, such as metronidazole. However, antibiotics are often undesirable because they may kill a broad range of the normal bacterial flora in the vagina, including the beneficial lactobacilli. This may cause secondary complications, because the lactobacilli keep various opportunistic pathogens in the vagina in check. The treatment may then necessitate a further treatment regimen, such as the ingestion of cultured dairy products to replace the lactobacilli in the body, as well as treatment by antifungal agents. Moreover, a rise in the level of anaerobes due to a lack of lactobacilli could further complicate the infection. Additionally, antibiotics, when used frequently within the vagina, may cause systemic toxicity through absorption from the vagina.

As such, a need currently exists for improved compositions for supporting and maintaining a healthy balance of microflora in the urogenital area and more particularly improved vaginal treatment compositions.

SUMMARY OF THE DISCLOSURE

It has now been surprisingly discovered that the growth of certain strains of Lactobacilli may be synergistically increased by administering a composition comprising two different carbon sources. The carbon sources may consist of a first saccharide and a second saccharide or an organic acid. Increasing the growth of beneficial lactobacilli may effectively inhibit the growth of pathogens associated with urogenital infections and help maintain a healthy microflora balance in the urogenital area. As such compositions comprising a first saccharide and a second saccharide or an organic acid are well suited for topical administration to the urogenital area of a female for support and maintain a healthy balance of microflora in the urogenital area. For example, providing a composition comprising a pentose and a disaccharide synergistically promotes the growth of *Lactobacillus* spp. without promoting growth of pathogenic bacteria such as *Escherichia coli* or *Gardnerella vaginalis*. Accordingly, in one embodiment the present invention provides a composition comprising a first therapeutic agent consisting of a pentose or a disaccharide and a second therapeutic agent selected from the group consisting of a non-digestible polysaccharide, an organic acid, a cyclodextrin, a pectic substance, a pentose or a disaccharide.

In other embodiments the present invention provides a composition comprising a disaccharide selected from the group consisting of lactulose, trehalose, rhamnose maltose, maltotriose, lactose and lactitol and a pentose selected from the group consisting of ribose, ribulose, arabinose, xylose, xylulose, and lyxose, methyl β-D-ribofuranoside and 2-deoxy-D-ribose. In a particularly preferred embodiment the disaccharide comprises from about 0.05 to about 1.0 wt/vol % and the ratio of disaccharide to pentose is from about 1:1 to about 1:10.

In still other embodiments the present invention provides a composition comprising a pentose selected from the group consisting of ribose, ribulose, arabinose, xylose, xylulose, and lyxose, methyl β-D-ribofuranoside and 2-deoxy-D-ribose and an organic acid selected from the group consisting of citric acid, lactic acid, methyllactic acid, phenyllactic acid, malic acid, mandelic acid, glycolic acid, tartronic acid, tartaric acid. In a particularly preferred embodiment the pentose comprises from about 0.05 to about 1.0 wt/vol % and the ratio of pentose to organic acid is from about 1:1 to about 1:10.

In yet other embodiments the present invention provides a composition comprising a first therapeutic agent selected from the group consisting of α-methyl-D-glucoside, β-methyl-D-glucopyranoside and salicin and a second therapeutic agent selected from the group consisting of a pentose, a disaccharide, a non-digestible polysaccharide, an organic acid, a cyclodextrin and a pectic substance.

In other embodiments the present invention provides compositions for administration to a user. Suitable formulations may include, for example, liquids, solutions, pastes or gels. Accordingly, in one preferred embodiment the present invention provides a formulation comprising a first therapeutic agent consisting of a pentose or a disaccharide and a second therapeutic agent consisting of an organic acid, a cyclodextrin, a pectic substance, a pentose or a disaccharide and a from about 0.05 to about 5.0 wt/vol of at least one gelling agent that includes gellan gum. In a particularly preferred embodiment the first therapeutic agent and the second therapeutic agent comprise from about 0.1 to about 2.0 wt/vol % and the ratio of the first therapeutic agent to the second therapeutic agent is from about 1:1 to about 1:10. In a particularly preferred embodiment the formulations may be topically applied to the urogenital area and are capable of supporting and maintaining a healthy balance of microflora in the urogenital area.

In yet other embodiments the compositions of the present invention may be applied to an applicator. Suitable applicators include a web, such as a wet laid tissue web or air laid web, gauze, cotton swab, transdermal patch, container or holder. Thus, in certain embodiments the composition may be applied to a nonwoven web, such as meltblown, coform, spunbond, airlaid, hydroentangled nonwovens, spunlace, bonded carded webs, and laminates thereof, as well as wet laid fibrous webs, such as tissue webs. Accordingly, in one embodiment the invention provides a therapeutic wipe comprising a nonwoven web and a composition disposed thereon, the composition comprising a pentose and a disaccharide.

In other aspects the compositions of the present invention may be administered to a user to maintain and support growth of *Lactobacillus* spp. and inhibit pathogens. Accordingly, in one embodiment the present invention provides a method for enhancing *lactobacillus* growth or activity in vivo comprising administering a composition comprising a first therapeutic agent consisting of a pentose or a disaccharide and a second therapeutic agent consisting of an organic acid, a cyclodextrin, a pectic substance, a pentose or a disaccharide.

Definitions

As used herein, the term "inhibit" generally means to reduce by a measurable amount or to prevent entirely.

As used herein the term "urogenital" refers to the vulva, vagina, urinary tract, bladder, and surrounding areas.

As used herein the terms "effective amount" and "therapeutic amount" is an amount sufficient to maintain and support a healthy balance of microflora. In fact, although not required, it may be desired to use a concentration that does not significantly affect or inhibit the growth characteristics of the normal vaginal flora or otherwise significantly irritate the vaginal tissue when used at inhibitory, noncytotoxic, or clinical concentrations. For example, the therapeutic agent(s) are desirably employed at a concentration of about 0.01 to about 20.0 wt/vol %, in some embodiments from about 0.1 wt/vol % to about 10.0 wt/vol %, in some embodiments from about 0.2 to about 5.0 wt/vol %, and in some embodiments from about 0.5 to about 4.5 wt/vol %. It should be understood that the dosage may vary with the age, condition, and type of infection suffered by the patient, and may be readily determined by one of skill in the art.

As used herein the term "therapeutic effect" refers to the ability of the compositions and formulations of the present invention to stimulate the growth of *L. crispatus* relative *E. coli* measured according to the therapeutic effect protocol described below. Generally therapeutic effect is expressed as a ratio of *L. crispatus* to *E. coli* and is desirably greater than about 30, more preferably greater than about 50 and more desirably greater than about 100.

As used herein, the designation "wt/vol %" or "wt/vol" refers to the value obtained by dividing the weight of a substance (in grams) by the volume of the solution (in milliliters), and then multiplying by 100.

As used herein the term "non-digestible polysaccharide" as used in the present invention refers to polysaccharides which are not or only partially digested in the intestine by the action of acids or digestive enzymes present in the human upper digestive tract (small intestine and stomach) but which are fermented by the human intestinal flora. For example, sucrose, lactose, maltose and maltodextrins are considered digestible. Preferably the non-digestible polysaccharide is a non-digestible neutral polysaccharide wherein more than 75% of the saccharides units are selected from the group consisting of glucose, fructose, galactose, mannose, ribose, rhamnose, arabinose, and xylose, preferably more than 85%, more preferably more than 95%, even more preferably more than 99%. Preferably the present non-digestible polysaccharide is a prebiotic polysaccharide that stimulates the growth and/or activity of one or a limited number of probiotic bacterial species in the colon.

As used herein the term "pentose" generally refers to a monosaccharide comprising a five-membered furanose ring.

Suitable pentoses may have the general formula $C_5H_{10}O_5$ such as, for example, ribose, ribulose, arabinose, xylose, xylulose, and lyxose, and isomers thereof. The term pentose also includes five-membered furanose rings reacted under acid conditions to form an acetal such as methyl δ-D-ribofuranoside. The term pentose also includes five-membered furanose rings derived from a pentose having the general formula $C_5H_{10}O_5$ by the loss of an oxygen atom such as 2-deoxy-D-ribose. Pentoses are preferably provided in the form of a five-membered furanose ring and therefore do not include sugar alcohols, which may have the same linear structure as pentoses, but are modified with one or more alcohol groups.

As used herein the term "pectic substance" generally refers to pectins, pectates, polygalacturonic acids, and mixtures thereof. Pectic substance are generally complex organic polysaccharides derived from the secondary cell wall of terrestrial plants. The polygalacturonic acid referred to herein is composed of repeating units of the galacturonic acid units are joined by α-(1→4) linkages. Pectin contains as its major component galacturonic methyl ester which is the methyl ester of a galacturan. However the galacturonic acid units are not fully esterified. The galacturan ethyl esters are linear molecules with molecular weights of approximately 30,000 to about 300,000.

As used herein the term "saccharide" generally refers to a polysaccharide, an oligosaccharide, or a monosaccharide. Frequently, references to a saccharide refers to a monosaccharide, such as a pentose, a disaccharide, such as lactulose, trehalose, rhamnose maltose, maltotriose, lactose and lactitol, a cyclodextrin, pectin, or a non-digestible polysaccharide.

As used herein the term "soluble" when having reference to a pentose, a disaccharide, an organic acid, a cyclodextrin, a pectic substance or a non-digestible polysaccharide means that the substance is at least soluble according to the method described by L. Prosky et al, J. Assoc. Off. Anal. Chem. 71, 1017-1023 (1988).

DETAILED DESCRIPTION OF THE DISCLOSURE

The present invention is related to compositions useful in maintaining and supporting healthy microflora. The compositions are particularly well suited for administration to the urogenital tract to support and maintain a healthy microflora. Additionally the compositions and formulations of the present invention may be useful in supporting and maintaining healthy microflora balance on skin, in the bladder or the gastro-intestinal tract. For example, maintenance and support of a healthy microflora may be achieved by topically administering a composition to the urogenital tract or other area of the body. In other embodiments the compositions of the present invention may be formulated for oral administration and orally administered to a patient to support and maintain healthy microflora in the gastro-intestinal tract.

Compositions useful in supporting and maintaining healthy microflora generally comprise a therapeutic amount of a first therapeutic agent and a therapeutic amount of a second therapeutic agent which may be a saccharide or an organic acid. The first therapeutic agent may be α-methyl-d-glucoside, β-methyl-D-glucopyranoside or salicin. In other embodiments the first therapeutic agent may be selected from the group consisting of a pentose, a disaccharide, a non-digestible polysaccharide, an organic acid, a cyclodextrin and a pectic substance.

Saccharides useful as therapeutic agents may be, for example, a pentose, a disaccharide, a cyclodextrin, a pectic substance or a non-digestible polysaccharide. Organic acids useful as therapeutic agents may be, for example, citric acid, lactic acid, methyllactic acid, phenyllactic acid, malic acid, mandelic acid, glycolic acid, tartronic acid, tartaric acid and gluconic acid. A particularly preferred organic acid is malic acid.

Urogenital treatment compositions of the present invention generally stimulate the growth of healthy, native, bacteria such as *Lactobacillus* spp. and may be administered in several forms to a user. For example, the urogenital compositions may be prepared as formulations for administration to a user or may be applied to a substrate, such as a wiping substrate, for administration to a user. Preferably the saccharides useful in the present invention are soluble to facilitate their formulation for administration to a user.

Surprisingly compositions comprising a first saccharide and a second saccharide or an organic acid synergistically promote the growth of healthy bacteria such as *Lactobacillus* spp. and more particularly *Lactobacillus* crispatus without promoting growth of pathogenic bacteria, such as *Gardnerella* (e.g., *Gardnerella vaginalis*) or *Candida* (e.g., *Candida albicans*), Accordingly, compositions of the present invention may be administered to a user to synergistically and selectively stimulate growth of lactobacilli without stimulating the growth of competing pathogenic bacteria. Thus, in-use, administration of a formulation comprising a first saccharide and a second saccharide or an organic acid may enhance the growth and colonization of healthy bacteria such as *Lactobacillus* spp. in the user, which thereby helps reduce the incidence of disease.

Accordingly, in a preferred embodiment, the urogenital composition comprises a first therapeutic agent and a second therapeutic agent wherein the composition synergistically effects the growth of *L. crispatus* over *E. coli* as measured using the therapeutic effect protocol described below. Preferably the composition yields a ratio of *L. crispatus* to *E. coli* greater than about 30, still more preferably greater than about 50 and still more preferably greater than 200, and even more preferably greater than about 300.

Generally compositions useful in the present invention comprise at least two therapeutic agents. For example, the first therapeutic agent may be α-methyl-d-glucoside, β-methyl-D-glucopyranoside or salicin and the second therapeutic agent may be selected from the group consisting of a pentose, a disaccharide, a non-digestible polysaccharide, an organic acid, a cyclodextrin and a pectic substance. Preferably the first and second therapeutic agents are different.

In certain embodiments the first therapeutic agent may comprise a saccharide and the second therapeutic agent may be an organic acid or a saccharide. For example, in one embodiment, the composition may comprise a pentose in combination with a disaccharide. Suitable pentoses may include ribose, ribulose, arabinose, xylose, xylulose, and lyxose, methyl β-D-ribofuranoside and 2-deoxy-D-ribose. Particularly preferred pentoses include arabinose and 2-deoxy-D-ribose. Preferably the pentoses have not been modified with one or more alcohol groups. Suitable disaccharides may be selected from the group consisting of lactulose, trehalose, rhamnose maltose, maltotriose, lactose and lactitol. Particularly preferred disaccharides are lactulose and trehalose. Accordingly, in one preferred embodiment the composition comprises arabinose or 2-deoxy-D-ribose and lactulose or trehalose. In other preferred embodiments the composition comprises lactulose or trehalose and a second therapeutic agent selected from the groups consisting of a pectic substance, a cyclodextrin, a non-digestible polysaccharides, a pentose and an organic acid.

In other embodiments the one of the therapeutic agents may be a pectic substance selected from the group consisting of pectins, pectates, and polygalacturonic acids. The pectic substance is preferably combined with a pentose, a disaccharide or a cyclodextrin to produce a composition useful in the present invention. Thus, in a particularly preferred embodiment the composition comprises a pectic substance and a pentose selected from the group consisting of ribose, arabinose, 2-deoxy-D-ribose and methyl β-D-ribofuranoside. In other embodiments the composition comprises a pectic substance and a disaccharide selected from the group consisting of lactulose, trehalose, rhamnose maltose, maltotriose, lactose and lactitol. In particularly preferred embodiments the composition comprises a first therapeutic component consisting of trehalose, lactulose, arabinose, or 2-deoxy-D-ribose and a second therapeutic component consisting of pectin.

In still other embodiments the therapeutic agent may be an organic acid. Organic acids useful in the present invention generally consist of mono- or polycarboxylic acids having one or more hydroxyl functional groups at least one of which is introduced into the α-position (i.e., on the carbon atom adjacent to the carboxyl functional group). Examples of particularly useful organic acids include citric acid, lactic acid, methyllactic acid, phenyllactic acid, malic acid, mandelic acid, glycolic acid, tartronic acid, tartaric acid and gluconic acid. In particularly preferred embodiments the organic acid is selected from the group consisting of citric acid, lactic acid, malic acid, glycolic acid and tartaric acid. In certain embodiments the organic acid may be provided with an appropriate counterion, such as calcium, sodium or magnesium. In particularly preferred embodiments the composition comprises a first therapeutic component consisting of trehalose, lactulose, arbinose, or 2-deoxy-D-ribose and a second therapeutic component consisting of an organic acid. In other preferred embodiments the composition comprises a first therapeutic agent and an organic acid selected from the group consisting of citric acid, lactic acid, malic acid, glycolic acid and tartaric acid, where the first therapeutic agent is trehalose, lactulose, arabinose, or 2-deoxy-D-ribose.

In other embodiments the therapeutic agent may be a cyclodextrin. Suitable cyclodextrins useful in the present invention include hydroxypropyl β-cyclodextrin, hydroxyethyl β-cyclodextrin, hydroxypropyl γ-cyclodextrin, hydroxyethyl γ-cyclodextrin, α-cyclodextrin and methyl β-cyclodextrin. Suitable cyclodextrins typically have to have an aqueous solubility of at least about 10% by weight. Alpha-cyclodextrin is a preferred cyclodextrin. In one embodiment the composition comprises a first therapeutic component selected from the group consisting of a pentose, a disaccharide or a pectic substance and α-cyclodextrin.

In still other embodiments the therapeutic agent may be a polysaccharide that is not digestible by humans. Suitable non-digestible polysaccharides include, for example, dextrin, inulin, fructo-oligosaccharide (FOS) and isomalto-oligosaccharides. In a particularly preferred embodiment the non-digestible polysaccharide comprises at least one beta-glycosidic (e.g., beta galactosidic or beta glucosidic) bond or at least one α-glycosidic (e.g., α-galactosidic or α-glucosidic) bond, and is non-digestible by a human digestive system, but can be digested by a bacterium. In one embodiment the bacterium is a *Bifidobacterium* spp. or *Lactobacillus* spp. Particularly preferred non-digestible polysaccharides include dextrin and inulin. In a particularly preferred embodiment the composition comprises dextrin or inulin and a second therapeutic agent selected from the group consisting of a pentose, a disaccharide, cyclodextrin and a pectic substance.

Generally compositions of the present invention comprise less than about 10.0 wt/vol % therapeutic agent. That is to say, that the total amount all therapeutic agents, such as pentose, disaccharide, pectic substance, cyclodextrin and organic acid, is generally less than about 10.0 wt/vol %. In particularly preferred embodiments the total amount of therapeutic agent is less than about 5.0 wt/vol % and still more preferably less than about 2.5 wt/vol %, such as from about 0.1 to about 2.0 wt/vol % percent and more preferably from about 0.2 to about 1.5 wt/vol %. For example, in one embodiment, the composition comprises from about 0.1 to about 2.0 wt/vol % disaccharide selected from the group consisting of selected from the group consisting of lactulose, trehalose, rhamnose maltose, maltotriose, lactose and lactitol and from about 0.1 to about 2.0 wt/vol % of a pentose, a pectic substance, a cyclodextrin or an organic acid.

Further, the first and second therapeutic agents should be provided in an amount sufficient to provide a synergistic effect when administered to a user. For example, where the composition comprises a pentose and an organic acid the pentose and organic acid are present in an amount sufficient to stimulate the growth of certain healthy bacteria such as *Lactobacillus bulgaricus, Lactobacillus acidophilus, Lactobacillus gasseri, Lactobacillus crispatus, Lactobacillus casei, Lactobacillus plantarum, Streptococcus faecium*, and *Streptococcus thermophilus*. Accordingly, in certain embodiments, the organic acid may range from 0.05 to 2.0 wt/vol %, such as from about 0.1 to about 1.5 wt/vol % and more preferably from 0.1 to 1.0 wt/vol % and the pentose may range from about 0.1 to about 2.0 wt/vol % and more preferably from about 0.5 to about 1.5 wt/vol %.

Generally compositions of the present invention comprise two different therapeutic agents and more preferably therapeutic agents having distinct molecular compositions. That is to say, that where one therapeutic agent is a disaccharide the second therapeutic agent is not a disaccharide or where one therapeutic agent is a pentose the second therapeutic agent is not a pentose. Particularly preferred combinations of therapeutic agents include, for example, a disaccharide and pentose, a disaccharide and a cyclodextrin, a disaccharide and a pectic substance, a pentose and a pectic substance, a pentose and an organic acid, a pectic substance and a non-digestible polysaccharide, a pentose or a disaccharide and a non-digestible polysaccharide, and a pentose and a cyclodextrin.

The amount of the first and second therapeutic agents may be varied relative to one another. For example, in certain embodiments, the ratio of the first therapeutic agent to the second therapeutic agent may range from about 1:1 to about 1:50, such as from about 1:1 to about 1:20 and more preferably from about 1:1 to about 1:5. Accordingly, in certain embodiments the composition may comprises from about 0.1 to about 2.0 wt/vol % disaccharide or pentose and from about 0.1 to about 1.0 wt/vol % organic acid, pectic substance or cyclodextrin.

The compositions of the present invention may be formulated for administration to a user. The composition is generally applied in the form of a douche formulation, spray, moisturizer, lotion, cream, jelly, liniment, ointment, salve, oil, foam, gel, film, wash, suppository, slow-releasing polymer, coating, liquid, vaginal capsule, vaginal tablet, vaginal film, vaginal sponge, vaginal ovule, etc. The composition may also be applied to a vaginal insert, tampon, wipe or pad, and then administered to the vagina. Formulations may comprise a first saccharide and a second saccharide or an organic acid, a solvent and optionally a dermatologically acceptable carrier. As used herein, "dermatologically acceptable carrier" generally refers to a carrier that is suitable for topical application to the keratinous tissue and is compatible with a prebiotic. The dermatologically acceptable carrier may be in a wide variety of forms such as, for example, simple solutions (water-based or oil-based), solid forms (e.g. gels or sticks) and emulsions.

Solvents may be either aqueous or non-aqueous. Water is a particularly preferred aqueous solvent. Non-aqueous solvents may include, for example, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the solvent constitutes greater than about 75 wt/vol %, more preferably greater than about 85 wt/vol %, and still more preferably greater than about 90 wt/vol %.

The compositions of the present invention are generally acidic, i.e., have a pH less than about 7.0 and more preferably less than about 6.0, such as from about 3.0 to about 6.0 and still more preferably from about 4.0 to about 5.0. In a particularly preferred embodiment the pH may be maintained at a mildly acidic level to correspond to normal vaginal conditions. For example, the pH may be within a range of from about 3.0 to about 6.0, in some embodiments from about 3.5 to about 5.0, and in some embodiments, from about 4.0 to about 4.5. The foregoing acid pH may also provide other benefits. For instance, when the composition is configured to form a gel, such as described below, a low pH level may also improve the gelation rate and gel strength to reduce the likelihood of leakage just after insertion of the composition into the vagina.

In view of the foregoing, in certain embodiments the composition may comprise a first therapeutic agent consisting of arabinose or 2-deoxy-D-ribose and a second therapeutic agent consisting of trehalose, lactulose, pectin, α-cyclodextrin or malic acid, wherein the total amount of therapeutic agent is from about 0.1 to about 2.0 wt/vol % and the ratio of the first therapeutic agent to the second therapeutic agent may range from about 1:1 to about 1:50, such as from about 1:1 to about 1:20 and more preferably from about 1:1 to about 1:5. In other embodiments the composition may have a pH from about 3.0 to about 6.0, more preferably from about 3.5 to about 5.0, and comprise first therapeutic agent consisting of trehalose or lactulose and a second therapeutic agent consisting of arabinose, 2-deoxy-D-ribose, pectin, α-cyclodextrin or malic acid, wherein the total amount of therapeutic agent is from about 0.1 to about 2 wt/vol % and the ratio of the first therapeutic agent to the second therapeutic agent may range from about 1:1 to about 1:50, such as from about 1:1 to about 1:20 and more preferably from about 1:1 to about 1:5.

In one particular embodiment of the present invention, for example, the composition is configured to rapidly form a gel when applied to the vagina. A "gel" is a colloid in which a disperse phase combines with a dispersion medium to produce a jelly-like, solid or semi-solid material. The gel may form in less than about one hour, in some embodiments less than about one minute, and in some embodiments, less than about 30 seconds. Among other things, such rapid gelation reduces the likelihood of leakage during use. In addition, because the gel may form intravaginally, it is more likely to retain its structure and shape over an extended period of time. In this manner, the gel may provide the prolonged release of a therapeutic agent that inhibits and/or treats vaginal infection. For instance, the gel may remain within the vagina for about 2 to about 48 hours to provide the desired effect.

Although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 to about 99 wt/vol % of the composition.

The disperse phase of the gel may be formed from any of a variety of different gelling agents, including temperature responsive ("thermogelling") compounds, ion responsive compounds, and so forth. Thermogelling systems, for instance, respond to a change in temperature (e.g., increase in temperature) by changing from a liquid to a gel. Generally speaking, the temperature range of interest is from about 25° C. to about 40° C., in some embodiments from about 35° C. to about 39° C., and in one particular embodiment, at the human body temperature (about 37° C.). Compositions that change state at about this temperature are useful because they will remain in a body cavity, for example, after they have been delivered. Any of a variety of thermogelling compounds that are capable of gelling when applied to the vagina may be used in the present invention. In some cases, thermogelling block copolymers, graft copolymers, and/or homopolymers may be employed. For example, polyoxyalkylene block copolymers may be used in some embodiments of the present invention to form a thermo-gelling composition. Suitable thermo-gelling compositions may include, for example, homopolymers, such as poly(N-methyl-N-n-propylacrylamide), poly(N-n-propylacrylamide), poly(N-methyl-N-isopropylacrylamide), poly(N-n-propylmethacrylamide), poly(N-isopropylacrylamide), poly(N,n-diethylacrylamide); poly(N-isopropylmethacrylamide), poly (N-cyclopropylacrylamide), poly(N-ethylmethyacrylamide), poly(N-methyl-N-ethylacrylamide), poly(N-cyclopropylmethacrylamide), and poly(N-ethylacrylamide). Still other examples of suitable thermogelling polymers may include cellulose ether derivatives, such as hydroxypropyl cellulose, methyl cellulose, hydroxypropylmethyl cellulose, and ethylhydroxyethyl cellulose. Moreover thermogelling polymers may be made by preparing copolymers between (among) monomers, or by combining such homopolymers with other water-soluble polymers, such as acrylic monomers (e.g., acrylic or methacrylic acid, acrylate or methacrylate, acrylamide or methacrylamide, and derivatives thereof).

The compositions of the present invention may also include an ion responsive compound. Such compounds are generally well known in the art, and tend to form a gel in the presence of certain ions or at a certain pH. For instance, one suitable class of ion responsive compounds that may be employed in the present invention is anionic polysaccharides. Anionic polysaccharides may form a three-dimensional polymer network that functions as the disperse phase of the gel. Generally speaking, anionic polysaccharides include polysaccharides having an overall anionic charge, as well as neutral polysaccharides that contain anionic functional groups.

Any of a variety of anionic polysaccharides capable of forming a gel when contacted with vaginal mucosa may be used in the present invention. Such gel-forming anionic polysaccharides are typically stable over the normal acidic pH values found in the vagina (e.g., from about 2.5 to about 5.5). For instance, some suitable examples of gel-forming anionic polysaccharides include natural gums, such as gellan gum and alginate gums (e.g., ammonium and alkali metal of salts of alginic acid); chitosan; carboxymethylcellulose, pectins, carrageenan, xantham gum, and derivatives or salts thereof. The particular type of anionic polysaccharide selected will depend, in part, on the nature of the composition and the other components used therein. For example, carrageenan is sensitive to particular types of cations, e.g., it typically gels in the presence of potassium but not sodium. Glycuronans, likewise, typically gel in the presence of divalent cations (e.g., Ca2+), but not monovalent cations (e.g., Na+). Xanthan gum may gel in the presence of divalent cations, but only at a relatively high pH.

Although any of the above-described anionic polysaccharides may be used in the present invention, gellan gum is particularly desired for use in the present invention, either alone or in combination with other gelling agents, because it is able to form a gel in the presence of a wide variety of different cations, including both monovalent and divalent cations. Gellan gum is intended to encompass any form of gellan, including native gellan, clarified gellan, deacylated gellan, nonacylated gellan (e.g., produced from genetically engineered bacteria), clarified gellan (the polysaccharide is fully or partially removed from the bacterial debris), chemically modified gellan, etc. Various types of gellan gums and methods for forming such gums are described in U.S. Pat. Nos. 4,326,052; 4,326,053, 4,377,636; 4,385,123, and 4,563,366. Suitable gellan gums are commercially available from a variety of different sources. For example, GELRITE™ gellan gum is available from Sigma-Aldrich Chemical Co. of St. Louis, Mo., and is produced from a naturally occurring polysaccharide after deacylation and clarification. Deacylated gellan is also available from CP Kelco U.S., Inc. of Chicago, Ill. under the name KELCO-GEL®.

Gellan gum may be either high or low acyl gellan. In the high acyl (or "native") form, two acyl substituents, acetate and glycerate, are present. Both substituents are located on the same glucose residue and, on average, there is one glycerate per repeat unit and one acetate per every two repeat units. In the low acyl form, the acyl groups may be wholly or partially removed through deacylation. The degree of deacylation of deacylated gellan gums may be at least about 20%, in some embodiments at least about 50%, and in some embodiments, at least about 75%. Alternatively, the low acyl gellan gum may simply be "nonacylated" in that it is formed without acyl groups by genetically engineered bacteria. Regardless of the manner in which they are formed, low acyl gellan gums generally have a gelation temperature within the range 30 to 50° C., which may be particularly well suited for use in the present invention so that it may gel at body temperatures of about 37° C., but remain stable at typical storage and transportation temperatures of about 25° C. In addition, low acyl gellan gums are also firm and elastic, and thus may retain their shape after delivery to the vaginal cavity.

In most embodiments the gelling agent(s) are present in an amount of from about 0.01 to about 10.0 wt/vol %, in some embodiments from about 0.05 to about 5.0 wt/vol %, and in some embodiments, from about 0.1 to about 1.0 wt/vol % of the composition.

If desired, a gelling composition may be provided in any desired form (e.g., liquid, powder, etc.). In fact, one particular benefit of the composition is that it may be administered as a liquid, which allows for the selection of a wider variety of administration techniques than would otherwise be available for a solid or semi-solid gel. One technique that may be employed includes dispensing the composition through a liquid applicator, such as a syringe or tube, into the vaginal cavity. The administered volume of the composition may constitute a single dose or two or more doses. Although not necessarily required, the composition of may also be sterilized prior to administration. Sterilization may be accomplished by any technique known in the art, such as using a gas (e.g., ethylene oxide), radiation (e.g., gamma), or heat (autoclaving). If desired, the composition may be subjected to one or more filtration steps prior to sterilization to help remove contaminants.

The urogenital compositions of the present invention may be applied to a suitable substrate, which in-turn may be used to apply the prebiotic to a user. Suitable applicators include a web, such as a wet laid tissue web or air laid web, gauze, cotton swab, transdermal patch, container or holder. Particularly preferred applicators include fibrous webs, including flushable and non-flushable cellulosic webs and nonwoven webs of synthetic fibrous material. Useful webs may be wet laid, air laid, meltblown, or spunbonded. Suitable synthetic fibrous material includes meltblown polyethylene, polypropylene, copolymers of polyethylene and polypropylene, bicomponent fibers including polyethylene or polypropylene, and the like. Useful nonwoven webs may be meltblown, coform, spunbond, airlaid, hydroentangled nonwovens, spunlace, bonded carded webs.

In certain embodiments, particularly those in which the urogenital composition is applied to a web, it may be desirable that the formulation provide certain physical attributes, such as having a smooth, lubricious, non-greasy feel; the ability to at least partially transfer from the web to the user's skin; the capability to be retained on the web at about room temperature; or the ability to be compatible with the web manufacturing process. In certain embodiments it is preferred that at least a portion of the composition is transferred from the tissue to the user's skin in use.

The composition may be applied to a web during formation of the web or after the web has been formed and dried, often referred to as off-line or post-treatment. Suitable methods of applying the composition to a web include methods known in the art such as gravure printing, flexographic printing, spraying, WEKO™, slot die coating, or electrostatic spraying. One particularly preferred method of off-line application is rotogravure printing.

In those instances where the composition is added to the web during formation of the web and prior to drying, it may be preferred to employ an application method that incorporates the composition on the surface of the web. One method of adding the prebiotic to the web surface is by applying the composition during creping of the tissue web. Surprisingly, the composition itself may be used as a creping composition or may be combined with other well-known creping compositions to apply the composition to a tissue web without significantly degrading important web properties such as strength, stiffness or sloughing.

Fibrous webs comprising a composition made according to the present disclosure can be incorporated into multi-ply products. For instance, in one aspect, a fibrous web made according to the present disclosure can be attached to one or more other fibrous webs to form a wiping product having desired characteristics. The other webs laminated to the fibrous web of the present disclosure can be, for instance, a wet-creped web, a calendered web, an embossed web, a through-air dried web, a creped through-air dried web, an uncreped through-air dried web, an airlaid web, and the like, and may or may not comprise a prebiotic.

In other embodiments, the composition could be applied to skin to promote, maintain, or enhance the balance of a healthy microflora. Application could be as a wipe, lotion, lubricant, cream, moisturizer, patch, or other topical application methods.

In certain embodiments the composition could be ingested to promote, maintain, or enhance the balance of a healthy microflora in the gastrointestinal tract.

Test Methods

Therapeutic Effect Protocol

Colonies of *L. crispatus* and *E. coli* were prepared as follows. A colony of *L. crispatus* was transferred to 7 ml MRS broth and incubated anaerobically (using BD GasPak EZ anaerobe container system with indicator) at 37° C. without shaking for 18-20 hours. A colony of *E. coli* was transferred to 5 ml TSB broth and incubated aerobically (shaking at 100 rpm) at 37° C. for 18-20 hours.

Colonies were then inoculated as follows. Bacterial cultures were gently vortexed and 1 mL of each culture was transferred to a corresponding 2.0 mL micro-centrifuge tube and then centrifuged for two minutes at 14,500 rpm. The cultural supernatant was removed and the cell pellet was re-suspended in 1 mL of 0.95% (wt/vol %) saline. The re-suspended colony was then centrifuged for two minutes at 14,500 rpms and the supernatant was removed. For *L. crispatus*, the pellet was re-suspended in 1 mL of 0.95% saline to achieve ~$10^7$-$10^8$ cfu/mL. For *E. coli* the pellet was re-suspended in 1 mL of 0.95% saline to achieve ~$10^8$-$10^9$ cfu/mL.

Media were prepared as follows.

TABLE 1

| Ingredients | g/L |
| --- | --- |
| Peptone | 15 |
| Tryptone | 10 |
| Yeast Extract | 10 |
| Tween 80 | 1 |

All of the ingredients in Table 1 were combined and the pH was adjusted to 6.5. The media were then autoclaved for 20 minutes at 125° C. To evaluate the effect of various therapeutic agents on the growth of bacteria the LAPT-g media, prepared as described above, was supplemented with various therapeutic agents to a final test concentration between 0.1 and 1.0%.

Five milliliters (5 mL) of each medium was transferred to a test tube in duplicates for subsequent inoculation. A master mixture of *L. crispatus* and *E. coli*, prepared as described above, was prepared in 1,000:1 ratio. Each (5 ml) test tube was inoculated with the master mixture to give $10^5$-$10^6$ total CFU *L. crispatus* and 100-1,000 total CFU *E. coli* per tube.

To establish a negative control, one tube was vortexed and 100 μL was removed to determine the initial cell concentrations by serial dilutions and plating (2 plates per dilution). *L. crispatus* is selected on MRS agar plates incubated anaerobically at 37° C. for two days. *E. coli* is selected on TSA plates incubated aerobically at 37° C. for one day. The co-cultures were incubated in an anaerobic container with BD GasPaks at 37° C. for 36 hours.

The effect of the carbon source on the ratio of *L. crispatus* to *E. coli* was measured 36 hours after inoculation. The co-culture tube was vortexed and 100 µL was removed to determine the final cell concentrations by serial dilutions and plating (2 plates per dilution). *L. crispatus* is selected on MRS agar plates incubated anaerobically at 37° C. for two days. *E. coli* is selected on TSA plates incubated aerobically at 37° C. for one day.

EXAMPLES

Inventive samples were prepared by supplementing LAPT-g media, prepared as described above, with various therapeutic agents as described in Table 2, below. The therapeutic effect of the formulation was then measured using the assay described above in the Test Methods section above. The therapeutic effect is summarized below as the ratio of *L. crispatus* to *E. coli*. The combinations of therapeutic agents that resulted in a ratio of *L. crispatus/E. coli* greater than the sum of the ratios of the individual therapeutic agents were considered synergistic.

The invention further provides in a second embodiment the composition of the first embodiment wherein the weight ratio of the first therapeutic and the second therapeutic agent is from about 1:1 to about 1:50.

Still further, the invention provides in a third embodiment the composition of the first or second embodiment, wherein the first therapeutic comprises from about 0.1 to about 2.0 wt/vol %, the second therapeutic agent comprises from about 0.1 to about 2.0 wt/vol % and the pH of the composition is from about 3.5 to about 6.0.

The invention also provides in a fourth embodiment the composition of any one of the first through the third embodiments where the first therapeutic agent is a pentose selected from the group consisting of ribose, ribulose, arabinose, xylose, xylulose, and lyxose, methyl β-D-ribofuranoside and 2-deoxy-D-ribose.

Additionally, the invention provides in a fifth embodiment the composition of any one of the first through the fourth embodiments where the first therapeutic agent is a disaccharide selected from the group consisting of lactulose, trehalose, rhamnose maltose, maltotriose, lactose and lactitol.

TABLE 2

| Sample No. | Therapeutic Agent (w/vol %) | CAS # | *L. crispatus/ E. coli* ratio |
|---|---|---|---|
| 1 | D-Trehalose (0.5%) + Pectin (0.5%) | 6138-23-4, 9000-69-5 | 653.3 |
| 2 | D-Trehalose (0.5%) + α-Cyclodextrin (0.5%) | 6138-23-4, 10016-20-3 | 100.4 |
| 3 | D-Trehalose (0.5%) + D-arabinose (0.5%) | 6138-23-4, 28697-53-2 | 197.3 |
| 4 | Pectin (0.5%) + α-Cyclodextrin (0.5%) | 9000-69-5, 10016-20-3 | 43.2 |
| 5 | Pectin (0.5%) + α-Methyl-D-Glucoside (0.5%) | 9000-69-5, 97-30-3 | 32.3 |
| 6 | 2-Deoxy-D-Ribose (0.1%) + Malic acid (0.1%) | 533-67-5, 6915-15-7 | 340 |
| 7 | 2-Deoxy-D-Ribose (0.1%) + D-Trehalose (0.9%) | 533-67-5, 6138-23-4 | 103.8 |
| 8 | 2-Deoxy-D-Ribose (0.1%) + Lactulose (0.1%) | 533-67-5, 4618-18-2 | 562.3 |
| 9 | D-Trehalose (0.1%) + Pectin (0.4%) | 6138-23-4, 9000-69-5 | 315.7 |
| 10 | Dextrin (0.1%) + Pectin (0.4%) | 9004-53-9, 9000-69-5 | 245.6 |
| 11 | Dextrin (0.1%) + Pectin (0.4%) | 9004-53-9, 9000-69-5 | 184.4 |
| 12 | D-Trehalose (0.5%) + P95 FOS (0.5%) | 6138-23-4, 9005-80-5 | 163.7 |
| 13 | D-Trehalose (0.4%) + HSI Inulin (0.6%) | 6138-23-4, 9005-80-5 | 126.5 |
| 14 | D-Trehalose (0.8%) + HSI Inulin (0.2%) | 6138-23-4, 9005-80-5 | 109.3 |
| 15 | Malic acid (0.1%) + Pectin (0.4%) | 6915-15-7, 9000-69-5 | 105.5 |
| 16 | Pectin (0.5%) + HSI Inulin (0.5%) | 9000-69-5, 9005-80-5 | 105.1 |
| 17 | Salicin (0.1%) + Pectin (0.4%) | 138-52-3, 9000-69-5 | 81.3 |
| 18 | Pectin (0.5%) + P95 FOS (0.5%) | 9000-69-5, 9005-80-5 | 65.8 |
| 19 | D-Trehalose (0.5%) + HSI Inulin (0.5%) | 6138-23-4, 9005-80-5 | 40.5 |
| 20 | α-Cyclodextrin (0.5%) + α-Methyl-D-Glucoside (0.5%) | 10016-20-3, 97-30-3 | 33.9 |
| 21 | 2-Deoxy-D-Ribose (0.1%) | 533-67-5 | 1.7 |
| 22 | α-Methyl-D-Glucoside (1%) | 97-30-3 | 3 |
| 23 | α-Cyclodextrin (1%) | 10016-20-3 | 6.5 |
| 24 | D-Arabinose (1%) | 28697-53-2 | 2.2 |
| 25 | Dextrin (0.1%) | 9004-53-9 | 0.9 |
| 26 | D-Trehalose (1%) | 6138-23-4 | 30.1 |
| 27 | HSI Inulin (1%) | 9005-80-5 | 0.5 |
| 28 | Lactulose (0.1%) | 4618-18-2 | 3.9 |
| 29 | Malic acid (0.1%) | 6915-15-7 | 30.7 |
| 30 | P95 FOS (1%) | 9005-80-5 | 1.1 |
| 31 | Pectin (0.5%) | 9000-69-5 | 9.5 |
| 32 | Salicin (0.1%) | 138-52-3 | 1.5 |

In view of the foregoing description and examples, the present invention provides, in a first embodiment, a composition comprising a first therapeutic agent consisting of a pentose or a disaccharide and a second therapeutic agent selected from the group consisting of a non-digestible polysaccharide, an organic acid, a cyclodextrin, a pectic substance, a pentose or a disaccharide wherein first therapeutic and the second therapeutic agent are different.

The composition of the first embodiment may be formulated as a liquid, a solution, a paste or a gel.

The invention further provides in a sixth embodiment the composition of any one of the first through the fifth embodiments where the second therapeutic agent is an organic acid selected from the group consisting of citric acid, lactic acid, methyllactic acid, phenyllactic acid, malic acid, mandelic acid, glycolic acid, tartronic acid, tartaric acid and gluconic acid.

The invention also provides in a seventh embodiment the composition of any one of the first through the sixth embodiments where the second therapeutic agent is a non-digestible polysaccharide selected from the group consisting of dextrin, inulin, fructo-oligosaccharide (FOS) and isomalto-oligosaccharides.

The invention further provides in an eighth embodiment the composition of any one of the first through the seventh embodiments where the first therapeutic agent is a pentose or a disaccharide and the second therapeutic agent is selected from the group consisting of pectin, α-cyclodextrin, dextrin, inulin and malic acid.

The invention also provides in a ninth embodiment the composition of any one of the first through the eighth embodiments wherein the composition synergistically promotes the growth of *L. crispatus* relative to *E. coli* such that the therapeutic effect is greater than about 30 and more preferably greater than about 50 and still more preferably greater than about 100.

The invention further provides in a tenth embodiment a composition comprising a first therapeutic agent consisting of a non-digestible polysaccharide and a second therapeutic agent selected from the group consisting of an organic acid, a cyclodextrin, a pectic substance, a pentose or a disaccharide.

The composition of the tenth embodiment may be formulated as a liquid, paste or a gel having a pH from about 3.0 to about 5.0 and comprising from about 0.1 to about 2.0 wt/vol % of the first therapeutic agent and from about 0.1 to about 2.0 wt/vol % of the second therapeutic agent.

In an eleventh embodiment the present invention provides a composition comprising a first therapeutic agent selected from the group consisting of α-methyl-d-glucoside, 3-methyl-D-glucopyranoside and salicin and a second therapeutic agent selected from the group consisting of a pentose, a disaccharide, a non-digestible polysaccharide, an organic acid, a cyclodextrin and a pectic substance. In a particularly preferred embodiment the first therapeutic agent is α-methyl-d-glucoside or salicin and the second therapeutic agent is pectin or α-cyclodextrin.

The invention also provides in an twelfth embodiment a method for maintaining a healthy microflora balance in the urogenital area, the method comprising topically administering to the urogenital area of a patient in need thereof the composition of any one of the first through the eleventh embodiments.

In still another embodiment the present invention provides a method for enhancing *lactobacillus* growth or activity in vivo comprising administering a composition of any one of the first through the eleventh embodiments to a patient in need thereof.

What is claimed is:

1. A composition comprising a first therapeutic agent comprising 2-Deoxy-D-Ribose and a second therapeutic agent comprising lactulose, wherein the composition synergistically promotes the growth of *L. crispatus* relative to *E. coli* such that the therapeutic effect is greater than about 30.

2. The composition of claim 1 wherein the weight ratio of the first therapeutic agent and the second therapeutic agent is from about 1:1 to about 1:50.

3. The composition of claim 1 wherein the first therapeutic agent comprises from about 0.1 to about 2.0 wt/v %, the second therapeutic agent comprises from about 0.1 to about 2.0 wt/v %.

4. The composition of claim 1 wherein the first therapeutic agent and the second therapeutic agent in combination comprise a total of about 5% wt/v %.

* * * * *